United States Patent
Hilaly et al.

(10) Patent No.: US 7,767,178 B2
(45) Date of Patent: Aug. 3, 2010

(54) REGENERATING MOLECULAR SIEVE ABSORBENTS USED FOR ALCOHOL DEHYDRATION

(75) Inventors: Ahmad K. Hilaly, Springfield, IL (US); Joseph R. Beggin, Warrensburg, IL (US)

(73) Assignee: Archer-Daniels-Midland Company, Decatur, IL (US)

(*) Notice: Subject to any disclaimer, the term of this patent is extended or adjusted under 35 U.S.C. 154(b) by 693 days.

(21) Appl. No.: 11/581,825

(22) Filed: Oct. 17, 2006

(65) Prior Publication Data

US 2007/0088182 A1    Apr. 19, 2007

Related U.S. Application Data

(60) Provisional application No. 60/727,654, filed on Oct. 18, 2005.

(51) Int. Cl.
*B01D 53/02* (2006.01)
(52) U.S. Cl. .................. 423/245.1; 423/210
(58) Field of Classification Search ............ 502/38, 502/39; 423/210, 245.1
See application file for complete search history.

(56) References Cited

U.S. PATENT DOCUMENTS

| | | | |
|---|---|---|---|
| 4,465,875 A | 8/1984 | Greenbank et al. |
| 4,784,868 A | 11/1988 | Young |
| 5,300,695 A | 4/1994 | Radlowski |
| 6,634,119 B2 | 10/2003 | Park et al. |

*Primary Examiner*—Edward M Johnson
(74) *Attorney, Agent, or Firm*—Craig G. Cochenour; Duane A. Stewart, III; Buchanan Ingersoll & Rooney PC

(57) ABSTRACT

A process for regenerating a molecular sieve absorbent bed used for dehydrating an organic solvent is disclosed. The process is illustrated by regenerating a molecular sieve bed used for dehydrating ethanol, which includes a dehydrating cycle where an ethanol/water vapor mixture is loaded onto the molecular sieve bed at a first temperature to absorb water and recover a substantially dehydrated ethanol vapor effluent. In a regeneration cycle, the bed is subjected to a temperature swing technique whereby a dried gas, such as dried $CO_2$, heated to at a second temperature greater than the first temperature, is passed over the molecular sieve bed, optimally in a counter current directional flow with respect to the dehydrating cycle. The process obviates the need for applying a vacuum pressure swing to regenerate the molecular sieve bed. Water and residual ethanol are removed with the $CO_2$ effluent and can optionally be condensed and combined with a feed input for a subsequent dehydrating cycle.

10 Claims, 5 Drawing Sheets

REGENERATING MOLECULAR SIEVE ABSORBENTS USED FOR ALCOHOL DEHYDRATION

CROSS-REFERENCE TO RELATED APPLICATION

This application is a utility application and claims the benefit of priority to U.S. Provisional Patent Application Ser. No. 60/727,654, filed on Oct. 18, 2005, entitled "Regenerating Molecular Sieve Absorbents Used For Ethanol Dehydration" having the same named applicants as inventors, namely, Ahmad K. Hilaly and Joseph R. Beggin. The entire contents of U.S. Provisional Patent Application Ser. No. 60/727,654 is incorporated by reference into this utility patent application.

BACKGROUND OF THE INVENTION

1. Field of the Invention

The invention relates generally to an improved process for the production of anhydrous ethanol, and in particular to methods to improve regeneration of molecular sieve materials used in ethanol dehydration processes.

2. Description of the Background Art

Anhydrous ethanol is widely used in industry as a solvent in the synthesis of paints, pharmaceuticals and intermediaries, cosmetics, perfumes, and other products, for example. Anhydrous ethanol is also an important component in alternative fuels, such as gasohol, when combined with gasoline and other fossil fuel distillate components to make fuel for motor vehicles and other combustion engine applications. Anhydrous ethanol can also be used as an important oxygenic additive in lead-free gasoline.

However, even small amounts of water in ethanol can lead to the formation of unwanted products under the conditions present in typical combustion engine combustion chambers, or other industrial synthetic processes. For example, 4.4% (wt) water and 95.6% (wt) ethanol will form an azeotrope under conditions greater than 78° C. temperature and exceeding 1.0 bar pressure, well below the threshold combustion conditions in an internal combustion engine. An azeotrope is a mixture having a constant boiling temperature and so is difficult to separate the components by distillation. Therefore, even a small amount of water contamination in anhydrous ethanol is extremely undesirable. Thus, the process of dehydrating or drying ethanol is a valuable process for producing anhydrous ethanol for use as a fuel or as a solvent in many industrial processes.

Traditional distillation to obtain anhydrous ethanol is a costly process requiring high amounts of energy to obtain pure anhydrous ethanol. Other processes that can be used to obtain anhydrous ethanol include azeotropic distillation, extractive distillation, and salt rectification. However, these processes still involve high energy distillation and its associated high energy costs to obtain anhydrous ethanol, resulting in a more expensive anhydrous ethanol product.

Adsorption purification of ethanol is a process requiring less energy than distillation processes to obtain anhydrous ethanol. Various methods using adsorption to various adsorbent matrices under various temperature and pressure conditions are used to obtain anhydrous ethanol without distillation. One method used for production of motor fuel grade ethanol uses a concentration swing to release adsorption of ethanol from a paper matrix. Another method uses a pressure or vacuum swing to increase adsorption of materials to a matrix, adsorbed material is then desorbed with a depressurization of the adsorption chamber. However, these methods still require large amounts of energy to effect the concentration or pressure swings to elute the anhydrous ethanol from the adsorbent, or require additional amounts of ethanol to be cycled through to maximize the dehydration of the ethanol product.

One adsorbent method of ethanol dehydration uses natural-derived particles as an adsorbent bed material to produce anhydrous ethanol. Examples of natural adsorbent bed materials include corn grits or wheat starch particles. One example of commercially available wheat starch particles is available under the trade name EnviroStrip (Archer Daniels Midland Co., Decatur, Ill., USA). The mechanism of adsorption of water by corn grits and Envirostrip starch particles involves hydrogen bonding of the water molecules with the hydroxyl groups on the starch chains (Rebar et al., 1984). Both types of starch chains, amylose and amylopectin, interact with water molecules in this manner. However, the amylopectin structures also physically trap water molecules in the matrix of chain branches (Rebar et al., *Biotechnology and Bioengineering*, 26, 513-517 (1984)). When the water molecules are trapped this way, some nearby —OH groups become unavailable for hydrogen bonding.

In spite of the advantages of using corn grits as a readily available and inexpensive adsorption dehydration matrix for ethanol/water mixtures, there are limitations of corn grits used as an adsorbent matrix. Corn grits may be regenerated by flushing with $CO_2$ gas, but generally have a limited working life in an ethanol dehydration process. Among the problems associated with use of corn grits (or wheat starch adsorbent particles) for ethanol dehydrating beds is that such natural products are fragile, tend to collapse, tend to agglomerate, and rapidly lose their capacity for water adsorption.

Another method used for ethanol dehydration is based on non-organic zeolite type materials that act as a molecular sieve beds. Unlike natural bed adsorbents, molecular sieve beds act as absorbents, where primarily, the water is differentially retained in the bed by virtue of being included in the pores of the bed matrix instead of being adsorbed onto surface features.

Molecular sieve beds require a different type of regeneration than natural adsorbent beds. The molecular sieve absorbents are regenerated in a process that uses anhydrous ethanol in combination with a "pressure swing" technique. In this technique the molecular sieve bed is regenerated by passing previously dehydrated ethanol vapor through the bed at a substantially lower pressure (i.e., a vacuum) than was used for loading the bed for the dehydration step. There are both high pressure and low pressure molecular sieve systems, but the regeneration of each involves use of a relative vacuum along with anhydrous ethanol in the regeneration step.

In one example high pressure system, the feed ethanol entering the bed is loaded at a temperature of 148.9° C. (300° F.) and a pressure of 473.7 kPa (68.7 psia). The anhydrous ethanol used to regenerate the column is loaded at the same temperature and a pressure of 13.8-20.7 kPa (2.0-3.0 psia). In another example high pressure system, the feed ethanol entering the bed is loaded at a temperature of 148.9° C. at a pressure of about 386.1 kPa (56 psia). The anhydrous ethanol used to regenerate the column is loaded at the same temperature and a pressure of 13.8-20.7 kPa (2-3 psia).

In one example low pressure system, the ethanol feed entering the column is loaded at a temperature of 93.3-115.6° C. (200-240° F.), preferably 104.4° C. (220° F.) at a pressure of 114.4 kPa (~16.6 psia). The anhydrous ethanol used to regenerate the column is loaded at the same temperature range and at a pressure of less than 13.8 kPa (2.0 psia). In another low pressure system, the ethanol feed entering the column is loaded at a temperature of 115.6° C. (240° F.) and a pressure of 137.9 kPa (20.0 psia). The anhydrous ethanol used to regenerate the column is loaded at the same temperature and a pressure of 17.2 kPa (2.5 psia). In yet another low pressure system, the ethanol feed entering the column is loaded at a temperature of 115.6° C. (240° F.) and pressure of 170.3 kPa (24.7 psia). The anhydrous ethanol used to regenerate the column is loaded at a temperature of 104.4° C. (220° F.) and a pressure of 10.3 kPa (1.5 psia).

There are significant drawbacks using a pressure swing technique, including high energy cost incident to drawing a substantial vacuum and waste of a portion of already dehydrated ethanol for regenerating a bed whose very purpose is to make the dehydrated ethanol.

There is therefore, a need for improved processes for producing anhydrous ethanol that reduce the energy requirements and waste incident to regenerating molecular sieve beds used for multiple dehydrations. The present teaching provides materials and methods that meet these and other needs and is applicable not only to dehydrating ethanol, but to dehydrating any organic solvent for which a molecular sieve bed is used for dehydration.

SUMMARY OF THE INVENTION

Described herein are novel processes and systems for regenerating molecular sieve beds used for the dehydration of organic solvents and novel methods for preparation of anhydrous solvents based on the same. The invention is exemplified by regenerating molecular sieve beds used for the preparation of anhydrous ethanol but is applicable for use in the preparation of other anhydrous organic solvents, particularly water miscible solvents and/or those that form azeotropes with water.

In one aspect, the processes for regenerating molecular sieve beds uses a temperature swing rather than a pressure swing to facilitate removal of water retained in the used molecular sieve bed. In the temperature swing technique, the molecular sieve bed is loaded with an organic solvent/water vapor at a first temperature, and regenerated at a second temperature greater than the first temperature. In another aspect, the methods use a heated gas rather than an anhydrous solvent to remove retained water. In particular embodiments, the methods use a combination of the temperature swing and the heated gas to regenerate the molecular sieve beds. The advantages of the invention include reduction in the amount of solvent needed to be recycled and reduction in the energy costs of regeneration.

Any heated gas capable of carrying water vapor may be used in the practice of the invention. In particular embodiments the gas is selected from carbon dioxide, nitrogen and/or a noble gas. In exemplary embodiments, the heated gas is $CO_2$.

In one exemplary embodiment for regenerating a molecular sieve bed used for ethanol dehydration, $CO_2$ is heated to 96° C. (205° F.) or higher and passed through the molecular sieve bed to obtain a vapor comprised of a mixture of the gas, water and residual ethanol removed from the bed. The vapor is optionally cooled upon exiting the sieve bed to separate the water and residual ethanol from the gas by condensation. In various embodiments, the exiting vapor and gas are cooled to less than about 50° C. or less than about 10° C. or to about 5° C. In one exemplary embodiment, the cooling is effected with a spray cooler. The resulting condensed liquid containing organic solvent and water may optionally be recycled by distillation and/or combination with a second solvent/water mixture that is subject to further dehydration over the molecular sieve bed.

The present teaching also permits use of lower temperatures for both loading and regenerating the molecular sieve beds than used in the prior art. In one exemplary embodiment for ethanol dehydration, the molecular sieve bed is loaded with the water/ethanol vapor at temperature of about 85° C. (185° F.) for dehydration and regenerated with the gas at a temperature of about 96.1° C. (205° F.). In a typical embodiment, the pressure is 110.3 kPa-124.1 kPa (16-18 psia) for both the loading step and the regeneration step. As a person of skill in the art can perceive, there is no substantial difference in the pressure between the loading and regeneration pressure steps.

DETAILED DESCRIPTION OF THE INVENTION

Figure 1:
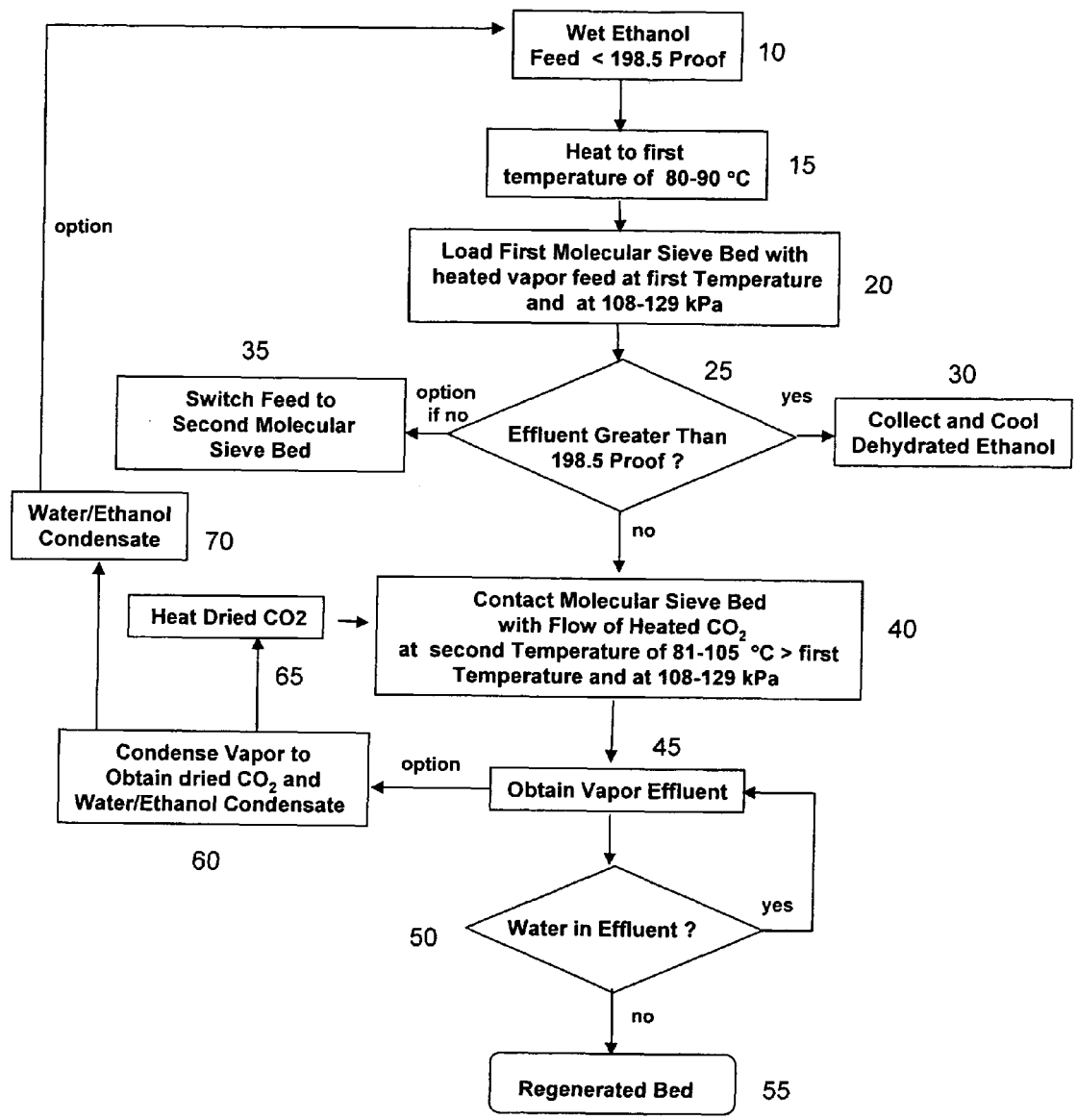
FIG. 1 shows a flow diagram of an example ethanol dehydrating process of the present teaching

The person of skill in the art will recognize various terms used in describing this invention as having the meaning ordinarily understood in the art, however, the terms "adsorption" and "absorption" are sometimes not properly differentiated in the art. Accordingly, the following definitions are intended to embrace the ordinary meaning of the terms without limitation, unless a specific limitation is incompatible with meanings provided herein, in which case the definitions provided herein control.

The term absorption refers to the process that includes mass based retention of a substance, such as for example, by molecular size inclusion, whereby molecules flow through a solid or semi-solid matrix through pores or channels or other internal structures and are thereby retarded in their flow through the matrix. In a mixture of molecules having different sizes, one class of molecules may be retained within the internal structures (absorbed) for a longer period than other molecules in the mixture that are relatively excluded from flow through such internal structures on the basis of size.

The term adsorption refers to a process that includes chemical based retention of substance, such as for example, by ionic or Van der Waals interactions. During a process of flow around and/or through a solid matrix adsorption occurs when certain molecules interact with surface features of the solid matrix and are thereby retarded in their flow. In a mixture of molecules having different structural features one class of molecules may differentially be bound to the surface features (adsorbed) to the matrix relative to a second class of molecules.

The term molecular sieve refers to a solid matrix having pores, channels, or other internal spaces of a size sufficient to selectively allow the infiltration or flow-through of a first class of molecules or solvents to the relative exclusion of a second class of molecules or solvents. The differential flow for the first class of molecule versus the second class of molecules results in differential absorption of the first class of molecules relative to the second class of molecules thereby affecting removal of the first class of molecules from a mixture initially containing the first and second classes of molecules. Molecular sieves may or may not also have adsorption properties, where at least one of the first or second classes of molecules may also differentially interact with surface features of the sieve, such as for example, by hydrophilic or hydrophobic interactions.

The term dry $CO_2$ or dry gas refers to a regeneration gas having less moisture content than the gas effluent from a molecular sieve at the beginning of a regeneration cycle. In alternative embodiments, the dry gas has a moisture content of less than 40%, less than 20%, less than 20%, less than 5% or less than 1%. In typical embodiments, the dry gas is what is ordinarily obtained from a supplier of a tank of the compressed gas.

The term saturated $CO_2$ or saturated gas refers to a regeneration gas having sufficient moisture content so that water will condense form the gas at some temperature below room temperature. In certain embodiments for saturated $CO_2$, water will precipitate from the gas at about 5° C.

The present teaching relates to regenerating molecular sieve beds used for dehydration of organic solvents primarily by absorption, however, one of ordinary skill in the art will recognize that both absorption and adsorption may occur when a mixture is resolved into its component parts when flowing through a molecular sieve bed matrix.

FIG. 1 is a flow chart that illustrates an exemplary embodiment of a method for dehydrating ethanol according to the present teaching. Wet ethanol, usually obtained by distillation from a fermentation broth having an ethanol concentration of less than 198.5 proof (less than 99.25% (v/v)) is provided at step 10. Typically, wet ethanol is obtained at 180-190 proof and most typically at about 184 proof. At step 15 the wet ethanol is heated to a first temperature sufficient to vaporize the mixture. Advantageously, and distinctively from the prior art, the load temperature is typically between 80 and 95° C., most typically about 85° C. At step 20 the heated ethanol vapor is loaded onto a molecular sieve bed at the first temperature and at a pressure of about 108.2 to 128.9 kPa (15.7-18.7) psia, which is only slightly above ambient atmospheric pressure (typically 101.3 kPa) such as is sufficient to urge a flow of the vapor through the molecular sieve bed at a desired flow rate.

As the heated ethanol vapor passes over the molecular sieve bed a portion of the water in the feed is preferentially absorbed in the molecular sieve bed and thereby removed from the flow of ethanol vapor. The feed ethanol vapor is passed over the bed until the dehydrated ethanol effluent falls below a desired specification as depicted in step 25 where the exemplified specification is at least 198.5 proof. If the dehydrated ethanol at step 25 meets the specification it is collected at step 30 to obtain the desired product. If however, the dehydrated ethanol drops below the specification in terms of water content, the collection from that sieve bed is halted and the sieve bed is subjected to the regeneration process at step 40. Optionally, as will be described in greater detail below, to provide a continuous uninterrupted dehydration process, the ethanol feed may be diverted to a tandem second molecular sieve bed at step 35 while the first molecular sieve bed is being regenerated by the temperature swing process of the present teaching at step 40.

The regeneration process entails heating a carrier gas to a second temperature sufficient to vaporize the water and any residual ethanol retained on the molecular sieve bed. The carrier gas need not contain, and preferably omits ethanol or water. In such embodiments, the gas is a "dried gas," which in typical embodiments, means the gas contains less than 5% volume of ethanol and/or water per volume of gas. However, the present teaching does not exclude use of a carrier gas that also includes a higher portion of ethanol and/or water (a wet gas) provided that the amount of water per unit volume of carrier gas is less than the amount of water per void volume of sieve bed. As used herein, "void volume" is the total volume of the sieve bed minus the volume of solid material. Any heated gas capable of carrying water vapor may be used in the practice of the invention. In particular embodiments, the gas is selected from carbon dioxide, nitrogen and/or a noble gas and for economic reasons, the heated gas is preferably $CO_2$.

The second temperature used for regeneration is greater than the first temperature used for loading. In typical embodiments, the second temperature is greater than the first temperature by at least 1° C., by at least 5° C., or by at least 10° C. In a typical economical process for dehydrating ethanol, the second temperature is about 81-105° C., most typically about 96° C. The term "about" as used herein, means within the degree of accuracy and precision of a typical instrument used to measure the temperature of gasses.

In the present teaching, the gas may be applied to the sieve bed at the same pressure range that was used to load the column with the ethanol feed. In the exemplary embodiment, both the load pressure and the regeneration pressure are 108-129 kPa. This contrast to the prior art, in which the regeneration of the molecular sieve bed entails applying a dehydrated ethanol vapor to the molecular sieve bed at a vacuum pressure of about 13.8-20.7 kPa. Prior to the present teaching, it was believed by those of ordinary skill in the art that due to the very small pore size of molecular sieve beds, efficient regeneration of such beds used for dehydrating organic solvents required both the pressure swing to a relative vacuum and the use of anhydrous solvent to remove the water in a solvent water mixture. Surprisingly however, it has been discovered that heated gas applied with, or more preferably without, such a pressure swing can be used to remove sufficient residual water from the molecular sieve bed to regenerate the bed without the need for using dehydrated solvent or substantial vacuum pressures.

While any gas capable of carrying water vapor is suitable for the methods taught herein, conveniently the carrier gas is $CO_2$ because it is an inexpensive and readily available as a by-product of an ethanol fermentation process. The vapor effluent (second effluent) from the flow of the regenerating heated gas is monitored for water content at step 50. While water remains in the second effluent above a specified value, (e.g., above 0.5%) the heated gas flow is continued. Optionally, the vapor effluent from the regeneration process may be collected and cooled at step 60 into an ethanol water condensate. The gas remaining after the condensation is thus dried or at least partially dried with respect to the effluent gas, and may be optionally reheated at step 65 and reused for regenerating the molecular sieve bed.

In an economically efficient process, the water/ethanol condensate is collected at step 70 and pooled with the feed stream of wet ethanol to be dehydrated therewith, thus minimizing waste and maximizing the recovery of dehydrated ethanol at step 30. When water in the gas effluent from the regenerating step is reduced to below the specified water content, the molecular sieve bed is regenerated and can be used for further dehydration of wet ethanol at step 10.

As mentioned in the Background section, in the prior art methods the wet feed ethanol is typically loaded onto the molecular sieve bed at higher pressures and temperatures than in the present teaching. In low pressure embodiments of the prior art, the load pressure is typically in the range of 114-170 kPa and the temperature is about 93 to 150° C. In the high pressure embodiments the pressure is in the range of 386-474 kPa and the temperature is about 149° C. Thus, in the prior art, the ratio of the load pressure and the regeneration pressure is at least 8 fold, and the difference in pressures is at least 100 kPa. While certain aspects of the present teaching can be practiced using higher load pressures, such large differences between the load and regeneration pressures are not required, nor is it required that the regeneration pressure be less than the load pressure. In fact, the regeneration pressure can be greater than the load pressure.

In the present teaching, there need not be any substantial difference between the load pressure and the regeneration pressures. By no "substantial difference" is meant that (i) the ratio of the load pressure to the regeneration pressure is less than 5 fold, less than 2 fold, less than 50%, or in typical embodiments, is less than 25% or less than 10% and/or (ii) the difference in load pressure and regeneration pressure is ±80 kPa, ±60 kPa, ±40 kPa, ±20 kPa, or in typical embodiments ±10 kPa. In the practice of the present methods, the load pressure and the regeneration pressure can be substantially the same, meaning the load pressure differs from the regeneration pressure by no more than ±50%.

Moreover, in the regeneration step, there need not be a vacuum relative to ambient atmospheric pressure (standard atmospheric pressure being 101.3 kPa (14.7 psia or 0 psig)). The regeneration cycle (as well as the load cycle) need only differ from ambient pressure by an amount sufficient to push (or draw) the flow of vapor through the bed at a suitable flow rate.

Hence, in certain embodiments, the regeneration pressure can be a positive pressure of 102 kPa or greater. In various economical embodiments, the positive pressure can be between 105 and 150 kPa as in the embodiment of FIG. 2 where the regeneration pressure is 108-129 kPa. In other embodiments, the positive pressure can be between 105 kPa and the pressure limit for functional operation of the molecular sieve bed, which is typically about 7000 kPa for zeolyte beds. In certain other embodiments the pressure can be a negative pressure relative to ambient sufficient to draw the gas through the molecular sieve bed. Advantageously, in such embodiments, the pressure need not be as low as the pressure swing vacuum used to draw dehydrated ethanol vapor through the bed as in the prior art. The pressure required by the present teaching to draw the carrier regeneration gas through the molecular support can be between 30 kPa and 98 kPa (i.e., 10-79 kPa less than standard atmospheric pressure). In various economical embodiments, the pressure can be 50-90 kPa., 60-90 kPa, 70-90 kPa or 50-90 kPa.

While use of the higher pressure ratios, pressure differences and pressures relative to ambient pressure within any of the foregoing ranges are within the scope of the present teaching, producing the higher ranges of pressure is generally costly, and not necessary for economical practices in the methods disclosed herein.

Likewise, while it is within the scope of the present teaching to use the higher load and regeneration temperatures of the prior art, the present teaching permits a more economical practice by using lower temperatures. In various embodiments for dehydrating ethanol for example, the load temperature of the ethanol/water vapor can be as low as 80-95° C., and more typically 85-90° C. The optimally economical load temperature will take into consideration bed performance, which varies by composition and manufacturer. A typical economical practice using a Type 3 zeolite molecular sieve bed according to the present teaching uses a load temperature of about 85° C. The regeneration temperature should be at least 1° C., at least 5° C., or at least 10° C. higher than the load temperature. In the exemplary embodiment, the regeneration temperature is about 11° C. higher than the load temperature. Accordingly, in various economical embodiments, the regeneration temperature can be as low as 81-105° C. and more typically 90-100° C. Taking into consideration bed performance, a typical economical practice uses a load temperature of about 96° C.

The productivity yield of dehydrated ethanol is higher using the heated regenerating gas method of the present teaching rather than other methods such as vacuum swing regeneration with anhydrous ethanol vapor as the regenerant. The methods disclosed herein offer significant economic benefit to the ethanol dehydration process. Molecular sieve beds regenerated by the present methods may last up to 10 times longer than corn grits beds, relieving the need for frequent repacking of the bed, which is a time consuming process.

Figure 2:
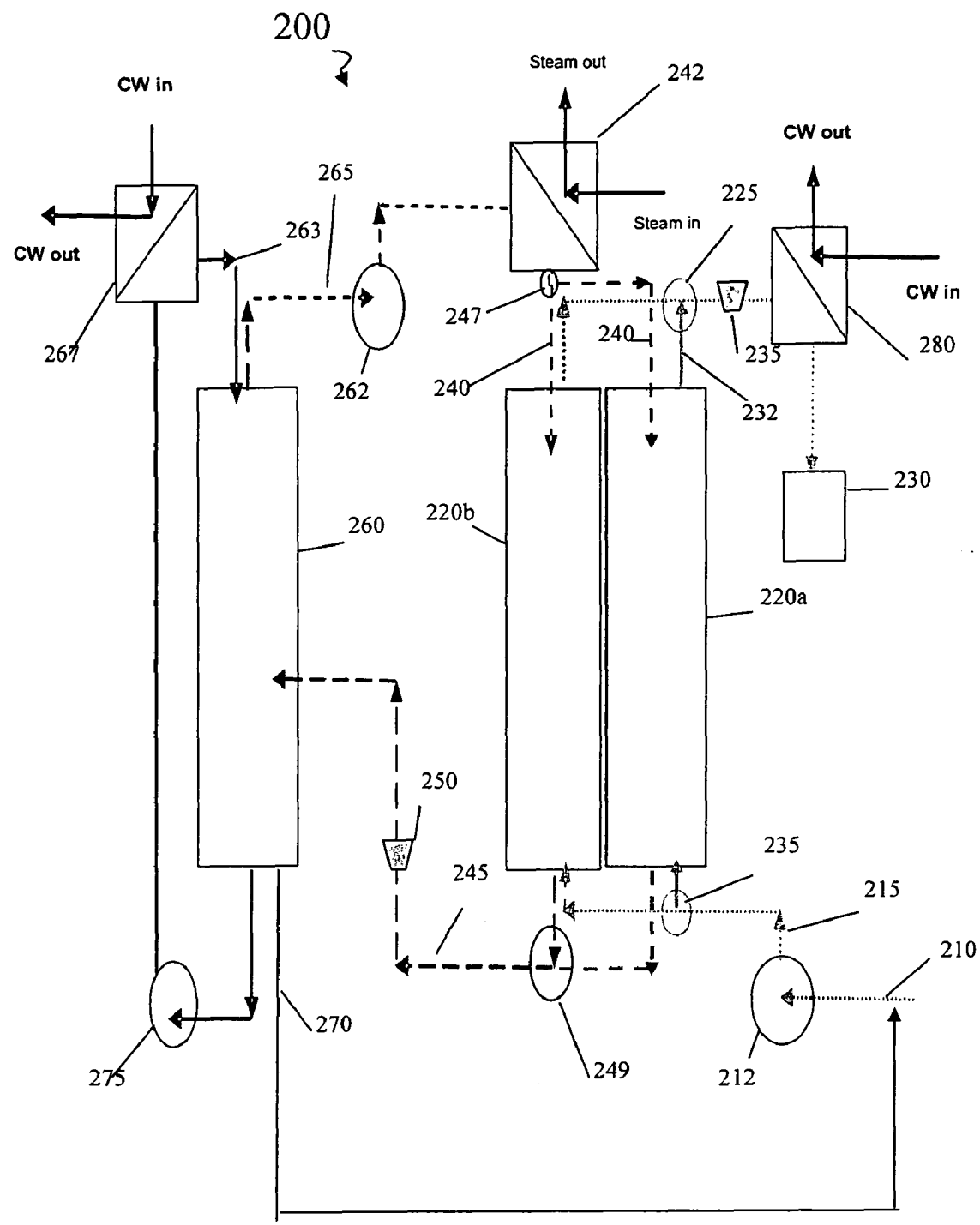
FIG. 2 illustrates an ethanol dehydrating and bed regenerating system of the present teaching.

FIG. 2 diagrammatically illustrates a production scale system 200 for producing dehydrated ethanol that incorporates the methods of the present teaching. In the system 200, a distilled aqueous ethanol feed stream 210 is heated to a vapor 215 at a temperature of 80-90° C. and pumped via vapor pump 212 into one of two molecular sieve absorbent bed columns 220a, 220b. In a typical practice, one of the absorbent beds 220a, 220b will be engaged in dehydrating the ethanol while the other is engaged in regeneration. The appropriate column 220a, 220b can be readily selected by mechanical control devices, for example by use of a feed valve 235. The vapor feed 215 is pumped upward through the molecular sieve bed 220a or 220b, which absorbs the water resulting in a dehydrated ethanol vapor effluent 232. Control valve 225 can be used to select which of the molecular sieve beds 220a, 220b from which to collect the dehydrated vapor effluent 232.

The water content of the dehydrated vapor effluent 232 can be monitored by appropriate monitoring instrumentation 235, such as a hygrometer, gas chromatograph, mass spectrometer or other indicator equipment configured for determining the water content of the dehydrated vapor effluent 232. Alternatively, the water content of the dehydrated vapor effluent 232 can be tested manually. So long as the dehydrated vapor effluent 232 meets the appropriate specification, it is passed into product cooler 280, which may for example, a water based condenser or other type of heat pump, to condense the dehydrated ethanol product which is collected in product container 230.

When the dehydrated vapor effluent 232 exceeds the specification for water content, the aqueous ethanol vapor feed 215 is switched to the other molecular sieve bed 220b or 220a, as the case may be, and the used molecular sieve bed is subjected to regeneration. Control valve 247 can be used to select the appropriate bed 220a, 220b for regeneration. A stream of dried $CO_2$ gas 265 is pumped via vapor recirculator 262 into a heater 242 to raise the temperature of the regenerating gas to 81-105° C., the regenerating temperature being selected to be higher than the load temperature of the original vapor feed 215. The heated $CO_2$ gas 240 is directed to the appropriate molecular sieve bed 220a or 220b to be regenerated by control valve 247. Notably, the direction of flow of the heated gas 240 is preferably opposite the direction of flow of the load vapor feed stream 215, which facilitates more efficient bed regeneration than when the direction of flow of the heated gas 240 is the same as the flow of the ethanol vapor feed 215. The heated regeneration gas 240 can be passed over the molecular sieve beds 220a, 220b at a positive pressure just above ambient pressure, obviating the need for a vacuum apparatus to reduce the pressure for effective regeneration.

The heated regenerating gas 240 passes over the molecular sieve bed 220a, 220b, which removes water and residual ethanol resulting in the second vapor effluent stream 245. A control valve 249 can be used to select the appropriate molecular sieve bed 220a, 220b from which to collect the second vapor effluent feed stream 245. Another monitor 250 may be used to detect the water content of the second vapor effluent stream 245. When the second vapor effluent stream 245 has a water content less than the specified value, the molecular sieve bed 220a. 220b is regenerated. Depending upon need and cycle time, in various embodiments, a water content of less than 5%, less than 0.5%, less than 0.1% or less than 0.01% can be used as a specification to indicate the molecular sieve bed 220a, 220b is regenerated. Unless indicated otherwise, % gas contents referred to herein are volume/volume percentages.

The second vapor effluent 245, which contains a mixture of water and ethanol is passed into a spray cooler or other form of condenser 260, where the water and ethanol in the vapor is condensed into a recovered ethanol/water liquid mixture 270. The coolant 263 used in the condenser is cooled by an appropriate cooler 267 prior to entering the condenser 260. The condenser 260 is fitted with a recirculating coolant pump 275 to pump the coolant 263 through condenser 260 and back to the cooler 267. The condensed ethanol/water liquid mixture 270 can be recovered and combined with the initial distilled ethanol/water feed stream 210 to be recirculated through the dehydration process while the cooled $CO_2$, now dried, can be reheated and recirculated through vapor recirculator 262 and heater 242 to be re-used as the regenerating gas 240.

As mentioned herein before, in an economically efficient industrial scale plant, continuous dehydration of ethanol is desired. To operate continuously, it is necessary to maintain a flow of the initial feed stream 210 of the ethanol/water to be dehydrated. To maintain the initial flow stream requires that at least one molecular sieve bed 220a, 220b always be available to receive the input stream of water/ethanol vapor 215. A dual molecular sieve bed system 220a, 220b illustrated in FIG. 2 can accomplish this goal only if the time required for regeneration is less than or equal to, the time required for dehydration. In practice however, when using the molecular sieve beds to produce dehydrated ethanol 230 with a specification of at least 198.5 proof starting from a typical distilled ethanol/water feed stream 215 of 184 proof, the time the molecular sieve bed can be used for dehydration is less than the time required to regenerate the bed for subsequent use. For example, in one embodiment, the load cycle for dehydration could continue for about 8 minutes before the effluent drops below specification, while the time required to regenerate the same molecular sieve bed to obtain the same dehydration capacity was about 16 minutes.

Figure 3:
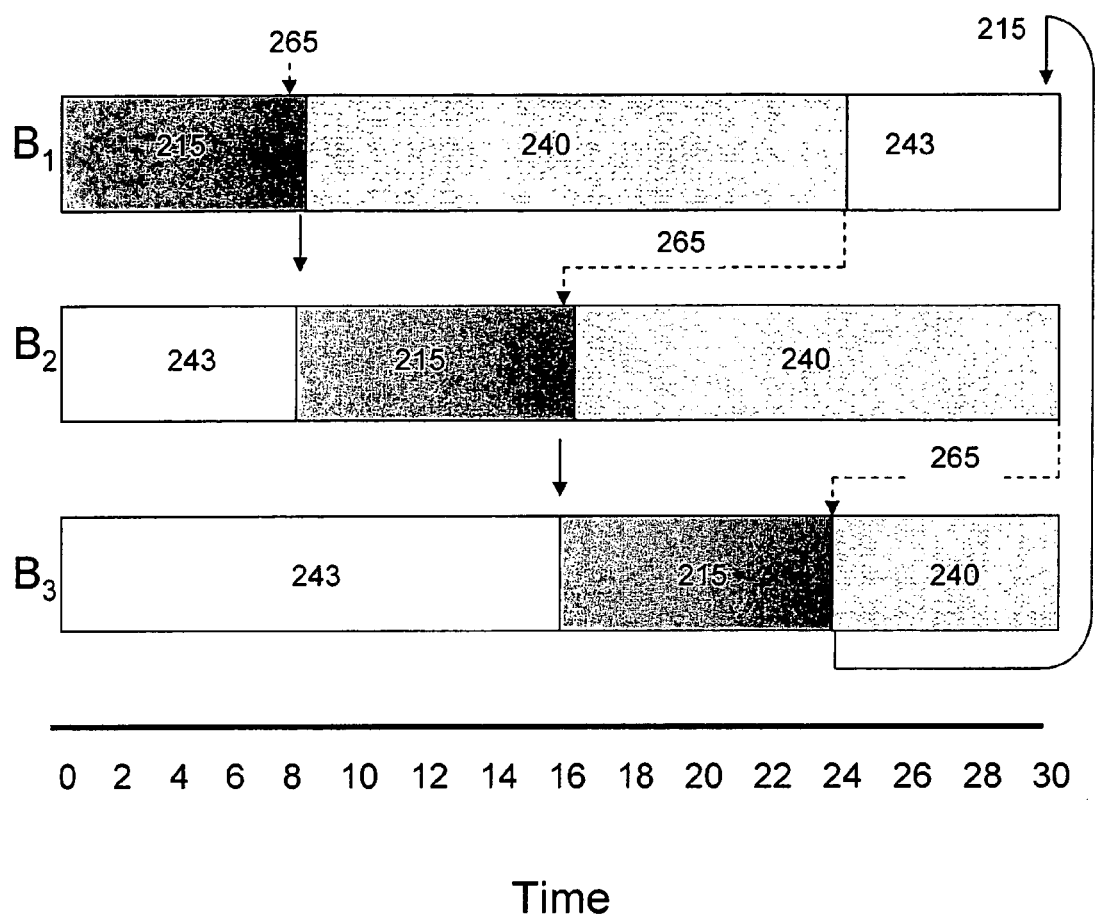
FIG. 3 schematically illustrates a continuous dehydration/regeneration scheme using three molecular sieve beds according to the present teaching.

One way to obtain continuous processing in light of such differential time requirements is to add a third molecular sieve bed to the system as schematically illustrated in FIG. 3 The input stream of ethanol water 215 is switched between three different sieve beds ($B_1$, $B_2$ and $B_3$) at staggered points in time selected so that one sieve bed is always available for the dehydration cycle while the other two sieve beds are at different points in the regeneration cycle. For example, using 8 minutes and 16 minutes as exemplary cycle times for dehydration and regeneration, respectively, at time equal zero minutes ($T_0$), the ethanol/water feed 215 is loaded onto molecular sieve bed $B_1$, bed $B_2$ has been regenerating for 8 minutes and bed $B_3$ is beginning the regeneration cycle. At $T_8$ the feed stream 215 is switched to molecular sieve bed $B_2$, bed $B_2$ had 16 minutes of regeneration, and bed $B_1$ is switched to the regeneration cycle 240 with dried $CO_2$ gas 265 and bed $B_3$ has been regenerating for 8 minutes. At $T_{16}$, the feed 215 is switched to bed $B_3$, bed $B_3$ has completed 16 minutes of regeneration, bed $B_2$ is switched to the regeneration cycle 240, and bed $B_1$ has been regenerating for 8 minutes. At $T_{24}$ minutes the feed stream is switched backed to bed $B_1$, after 16 minutes of regeneration bed $B_3$ is switched to the regeneration cycle 240, and bed $B_2$ has been regenerating for 8 minutes. The switching cycle continues in this manner so that there is always one molecular sieve bed ready to be engaged for dehydration.

There are also ways to operate a continuous process using only dual molecular sieve beds. For example, one way is to slow the flow rate of the input stream 215 so that the time used for the dehydration cycle matches the time required for regeneration. Because the regeneration step is usually rate limiting, the flow rate of the regenerating gas 240 is typically set to the maximum rate tolerated by the molecular sieve bed during the regeneration cycle. For the dehydration cycle, slower flow rates generally lead to more distinct separation zones. Thus, the dehydration cycle can be slowed to match the regeneration cycle without adversely affecting dehydration performance. However, a commercial draw back of slower input flow rates is reduced yield per time period of operation.

Another way to accomplish compatible regeneration and dehydrating times is to modify the specification for the distilled ethanol/water input stream 215. Thus for example, by further distillation, the input stream could be specified to be at least 188 proof instead of 184 proof. The use of a higher grade input stream 215 means the molecular sieve beds needs to absorb less water and therefore can be used for a longer period of time before the dehydrated effluent 232 falls below specification. However, the use of a higher grade input will usually incur additional energy and/or materials costs for installing more sophisticated distillation equipment to prepare the initial feed 215.

The present teaching may be practiced with any molecular sieve bed material capable of differentially absorbing water in comparison to ethanol. While the preferred molecular sieve bed materials are aluminum silica based zeolites, other sieve bed materials such as polymer based sieves having pore sizes large enough to include water and small enough to exclude ethanol may also be used. With respect to zeolites, there are several commercially available sources of zeolite molecular sieve beds commonly used in ethanol dehydration that are suitable for the practice of the present teaching. Examples include, but are not limited to:

UOP Molecular Sieve from UOP LLC, (Des Plaines, Ill. USA) Molecular Sieve Type 3A; ° Cylinder shape. (~⅛" dia.; ¼ to ⅜" length); ° Chemical Name: Sodium/Potassium Aluminosilicate; Synonyms: Zeolite);

Sylobead 564ET3A and 562Et from Grace Davison (W.R. Grace & ° Co.-Conn., Baltimore, Md. USA). Sylobead 562Et: (4×8 mesh), is a highly porous, high performance, Type 3A molecular sieve in spherical form, in which the pore openings have a diameter of approximately 3 angstroms and sphere size is a nominal ⅛" diameter. Sylobead 564Et: (8×12 mesh), is a highly porous, high performance, Type 3A crystalline aluminosilicate in spherical form; the pore opening in the crystals have a diameter of approximately 3 angstroms controlled by a high exchange rate of the potassium cation which minimizes coabsorption of ethanol and sphere size is a nominal 1/16" diameter;

Type Z Grade from Sphinx (Sphinx Adsorbents, Inc. Springfield Mass. USA). Type Z Molecular Sieve Grade 3A-8 (4×8 mesh) or Grade 3A-12 (8×12 mesh). These are spherical shaped, with an apparent density 47 lbs/ft$^3$ a pore size of 3 angstrom, cation type K, heat of adsorption 1800 BTU/lb water, water content as shipped 1.5% (by weight), maximum absorptive capacity 21% (by weight), specific heat 0.23 BTU/lb/° F.;

Z3-03 from Zeochem (Louisville, Ky., USA). Zeochem Z3-03 either in 8×12 mesh or 4×8 mesh, spherical shaped, chemical name: $Mx/n[(AlO_2)x(SiO_2)y]+H_2O$, chemical formula: synthetic sodium potassium or calcium aluminosilicate, chemical family: molecular sieve Zeolite.

Type 3A Zeolite molecular from Adcoa Adsorbents & Dessicants ° Corp. (Los Angeles, ° Calif., USA), which is available in potassium and in crystalline form having the following specifications: 3 angstroms nominal pore size, simple cubic crystal structure, 21%(wt) equilibrium water capacity, 44-46 lbs/cu. ft. bulk density, 10 lbs crush strength (bead), 1800 BTU/lb $H_2O$ heat of adsorption (max), and 10.5 pH of slurry.

For aid to one of ordinary skill in the art, the adsorption equilibria and kinetics of ethanol-water mixtures in molecular sieves have been quantified in molecular sieve systems such as crystalline zeolyte 3A, 4A, NaX, NaY, in both liquid phase and vapor phase (Guan et al., *Separation and Purification Technology*, 31, pp. 31-35 (2003), which is incorporated herein by reference.

As described in Examples 1 to 4 below, several molecular sieve absorbent materials were compared to natural dehydration bed adsorbent materials to demonstrate the regeneration methods of the present teaching. Corn grits adsorbent materials were used according to the following granulation parameters: (results are an average of four Certificates of Analysis): US #10: 0.3% greater than 2 mm (0.0787 inches); US #16: 87.3% greater than 1.19 mm (0.0469 inches); US #20: 10.9% greater than 0.841 mm (0.0331 inches); thru US #20 1.5% less than 0.841 mm (0.0331 inches).

EXAMPLES

The following examples demonstrate the invention in greater detail. These examples are not intended to limit the scope of the present teaching in any way.

Example 1

Molecular Sieve Screening for Dehydration ° Capacity

Four different molecular sieve absorbents were studied. Many of the initial tests involved regenerating the molecular sieves with dry $CO_2$. The molecular sieve absorbents tested were: UOP mole sieve; Grace Davison 564ET 3A; Sphinx Type Z Grade 3A-8; Zeochem Z3-03. All absorbents were 4×8 mesh spherical beads. Jacketed glass columns were used to hold the absorbents.

Column size is: 25 mm inside diameter×600 mm length

The system was operated as follows for each cycle: the feed cycle was run for 8.25 min and regeneration cycle for 13.75 min, respectively. The feed ethanol (92% ($^v/_v$)), was vaporized by pumping through stainless steel tubes, submerged in a heated oil bath and applied to the bed at a temperature about 85° C. The product ethanol was recovered by condensing discharge vapor in a heat exchanger. ° Composite samples of this condensed ethanol were tested for percent moisture.

Failure of the molecular sieve was determined when the product ethanol dropped below a specification of 198.5 proof (99.25% ($^v/_v$)). To screen the molecular sieve, the feed was started at a "low" feed rate for one day, to insure equilibrium, and then it was sampled. The ethanol feed rate was increased and the process repeated. The regeneration gas used, temperature and flow rate for all adsorbents were identical and unchanged during testing. Capacity of adsorbent should be determined from this test. Results are in Table 1. Product proof failure is indicated by bold highlight. Duplicate data points are result of operating, more than one day, at the selected conditions. The Grace Davison and Zeochem molecular sieves had greater capacity and merited further study.

TABLE 1

Demonstration of Ethanol Dehydration by Zeolite material using thermal swing regeneration

| Bed Volumes | Feed Rate (mL/min) | Product Ethanol Proof | | | |
|---|---|---|---|---|---|
| | | UOP | Grace | Sphinx | Zeochem |
| 20.4 | 1.4 | 199.8 | 199.8 | 199.8 | 199.8 |
| 20.4 | 1.4 | 199.8 | 199.8 | 199.6 | 199.8 |
| 24.8 | 1.7 | 199.8 | 199.8 | 199.8 | 199.8 |
| 29.1 | 2.0 | 199.8 | 199.8 | 199.8 | 199.8 |
| 29.1 | 2.0 | 199.8 | 199.8 | 199.8 | 199.8 |
| 33.5 | 2.3 | 199.0 | 199.8 | 195.6 | 199.8 |
| 33.5 | 2.3 | 198.6 | 199.8 | 196.0 | 199.2 |
| 33.5 | 2.3 | 197.8 | 199.8 | 197.4 | 199.8 |
| 36.4 | 2.5 | 196.0 | 199.8 | 195.0 | 198.4 |
| 38.6 | 2.65 | 194.6 | 199.4 | 193.4 | 197.0 |
| 40.8 | 2.8 | 193.0 | 198.4 | 192.0 | 195.8 |

To compare against the performance of natural adsorbents, the ENVIROSTRIP™ adsorption matrix (Archer Daniels Midland ° Company, Decatur, Ill., USA), which is a wheat starch media, and conventional corn grits were assessed against the performance of the Grace Davison, and Zeochem molecular sieves according to the same methods and criteria for product proof failure. The results are shown in Table 2. The molecular sieve adsorbents, have greater capacity for water, when compared with the same volume of natural adsorbents.

TABLE 2

Comparison of zeolite adsorbents and/with natural ingredients

| Bed Volumes Fed | Feed Rate (mL/min) | Product Ethanol Proof | | | |
|---|---|---|---|---|---|
| | | EnviroStrip | Grace | Corn Grits | Zeochem |
| 29.1 | 2.0 | 198.1 | 199.8 | 199.1 | 199.8 |
| 34.9 | 2.4 | 194.8 | 199.6 | 197.1 | 199.5 |
| 36.4 | 2.5 | 197.7 | 199.8 | 198.1 | 199.8 |

Example 2

Adsorbent Bed Regeneration with Saturated $CO_2$

To simulate industrial conditions for the ethanol dehydration process, the molecular sieves and corn grit beds were regenerated with saturated $CO_2$. The performance of the bed regeneration improved with decreasing saturation temperature of the $CO_2$ regeneration gas, i.e., the lower the $CO_2$ temperature the more water that could be removed from the ethanol. ° Comparison data of various molecular sieves, Envirostrip and corn grits (regenerated with saturated $CO_2$) and using an ethanol feed of 184 proof are shown in Table 3. These tests used identical columns and followed the test protocol used for Example 1, Table 1. Product proof failure, i.e. when percent moisture content exceeded 0.75% (v/v) is indicated in bold. The plot shown in FIG. 5 demonstrates the increased capacity of the molecular sieve.

$CO_2$ is a gas that is generated during the fermentation of ethanol, which makes it a readily available, non-flammable gas, perfectly suited for this process. During a typical industrial regeneration cycle, the $CO_2$ vapor effluent, leaving the adsorbent bed is cooled to precipitate moisture from the carbon dioxide. By cooling the vapor to 5° C. (41° F.) most of the moisture in the $CO_2$ condenses and can be separated from the gas. After this separation, the gas is heated to a temperature near 96° C. (205° F.) and recycled through the absorbent bed, removing the moisture from the bed. Thus, the absorbent bed was regenerated sufficiently to be useful for absorbing moisture for the next ethanol feed cycle with the same gas source used to regenerate the previous bed.

Adsorbents regenerated with saturated $CO_2$, have lower adsorbent capacity. The saturated recycle gas, will always contain a small percentage of water. Moisture flows from a source of high moisture to low moisture. If the saturated $CO_2$ has 10% moisture and dry $CO_2$ has 0%, the driving force that moves moisture from high to low source, is reduced by this amount. The difference can be seen comparing FIG. 4 (dry $CO_2$ regeneration) and FIG. 5 (saturated $CO_2$ regeneration). With dry $CO_2$ regeneration, Envirostrip product moisture reaches 1% after ~35 bed volumes feed ethanol and ~28 bed volumes with saturated $CO_2$ regeneration. Similarly, the corn grit product moisture is 1% after ~50 bed volumes feed (dry $CO_2$) and ~36 bed volumes (saturated $CO_2$ regeneration).

TABLE 3

Saturated $CO_2$ adsorbent bed regeneration.

| Bed Volumes Fed | Feed Rate (mL/min) | Product Ethanol Proof | | | |
|---|---|---|---|---|---|
| | | EnviroStrip | Grace | Corn Grits | Zeochem |
| 27.7 | 1.9 | 196.3 | 198.8 | 198.2 | 198.7 |
| 28.4 | 1.95 | 197.7 | 199.1 | 198.8 | 199.1 |
| 29.1 | 2.0 | 197.3 | 198.8 | 198.2 | 198.8 |
| 29.1 | 2.0 | 198.0 | 199.1 | 198.8 | 199.0 |
| 33.5 | 2.3 | 196.4 | 198.8 | 197.4 | 198.3 |
| 34.2 | 2.35 | 195.5 | 198.6 | 196.2 | 197.4 |
| 34.9 | 2.4 | 194.7 | 198.7 | 196.9 | 198.1 |

With the Zeochem molecular sieve—breakthrough occurs at ~2.3 mL/min (Table 3 above) and ~2.5 mL/min (Table 1). This molecular sieve has increased capacity when regenerated with dry $CO_2$. With the Grace Davison molecular sieve—breakthrough was not reached, during testing that generated data for Table 3. The product proof at 2.4 mL/min feed rate is 198.7 proof (Table 3). However, the product proof is 199.8 at a feed rate of 2.5 mL/min when regenerated with dry $CO_2$ (Table 1)—lower product moisture with greater feed rate indicates increased capacity with dry regeneration gas. Regenerating the molecular sieve with dry $CO_2$ increases capacity and performance, but dry $CO_2$ is more expensive to generate than $CO_2$, saturated at 5° C. The performance of the molecular sieves exceed the natural adsorbents with saturated $CO_2$.

The natural adsorbents and zeolites were compared with a breakthrough test. This test has all adsorbents regenerated under identical conditions. Feed is started to each column and product samples were collected at timed intervals. Breakthrough of adsorbent is determined to be when the product sample moisture exceeds 0.75% ($^v/_v$). Results are plotted in FIG. 5. The Envirostrip and corn grits reached breakthrough with less than forty bed volumes ethanol fed to the columns. Comparing FIG. 4 (regenerating with dry $CO_2$) and FIG. 5 (regenerating with saturated $CO_2$), the molecular sieve did not reach breakthrough, during the sampling period of either test.

Example 3

$CO_2$ Regeneration of Extended Length Molecular Sieve Beds with Dried Gas

Columns were assembled to achieve a seven foot (2.1 meter) adsorbent bed depth to more accurately model an industrial scale adsorbent bed.

A typical Ethanol Dehydration cycle in an industrial plant might be 8.25 minutes ethanol feed and about 13.75 minutes carbon dioxide regeneration cycle. Pilot columns were operated around-the-clock using the same cycle times. A breakthrough test was used to determine/compare the dehydrating capacity.

Since equipment had been operating around-the-clock, before the Breakthrough Test, absorbent was regenerated for 30-90 minutes. Regenerating the absorbent by passing heated $CO_2$ at a temperature of about 96° C. over the bed in reverse direction to feed ethanol, through the molecular sieve to remove moisture. This is the extended regeneration cycle.

A breakthrough test uses a constant feed rate, of 92% v/v ethyl alcohol, to the absorbent. Individual product samples of ethanol were collected at timed intervals and the percent moisture was measured for each sample. "Breakthrough" occurred when the percent water in product exceeded 0.75% ($^v/_v$). The greater the time that ethanol could be fed to a column before product breakthrough, the more capacity the absorbent possessed.

Figure 6:
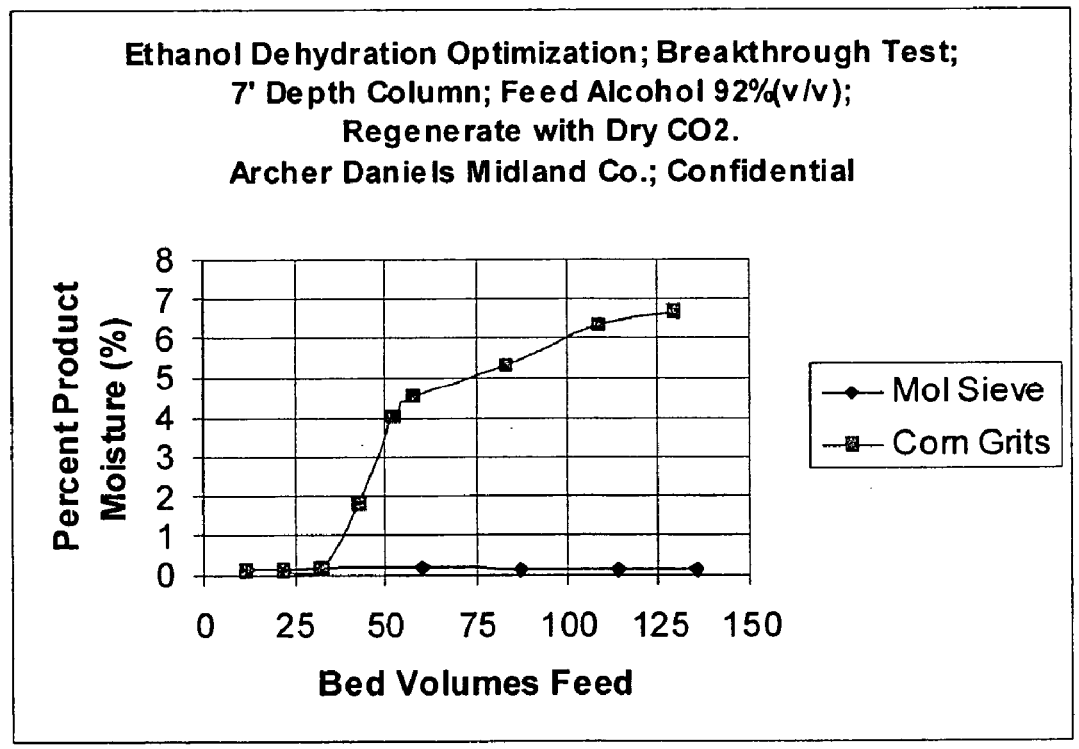
FIG. 6 shows a plot of anhydrous ethanol percent moisture (v/v) vs. bed volumes equivalents, comparing a molecular sieve bed to the corn grits adsorbent bed using dry $CO_2$ as the regenerating gas.

FIG. 6 illustrates the increased capacity, for water adsorption compared to molecular sieves and corn grits.

Example 4

Extended Length Ethanol Dehydration Bed ° Columns Operating with Saturated $CO_2$ Regenertion To further model the industrial equipment—the extended length dehydration bed was operated by regenerating with saturated carbon dioxide. Around-the-clock data is compiled in Table 4. Table 4 also lists a Product Yield %, which was calculated as the weight percent of product ethanol recovered from the feed ethanol.

TABLE 4

Extended length dehydration bed column with saturated, at 5° C., CO₂ regeneration.

| Days In Use | Molecular Sieve | | | Corn Grits | | |
|---|---|---|---|---|---|---|
| | Feed Rate (mL/min) | Product Proof | Product Yield (%) | Feed Rate (mL/min) | Product Proof | Product Yield (%) |
| 20 | 11.54 | 198.6 | 88.2 | 7.87 | 198.7 | 61.9 |
| 19 | 11.55 | 198.6 | 89.1 | 7.87 | 198.5 | 65.8 |
| 18 | 11.55 | 198.8 | 90.1 | 8.41 | 198.4 | 68.1 |
| 17 | 11.47 | 199.0 | 89.7 | 8.39 | 198.5 | 70.7 |
| 16 | 10.97 | 198.7 | 91.0 | 8.01 | 198.4 | 69.2 |
| 15 | 10.98 | 198.8 | 82.6 | 8.04 | 198.5 | 64.5 |
| 14 | 11.05 | 198.9 | 90.2 | 8.11 | 198.5 | 69.7 |
| 13 | 10.97 | 198.7 | 79.2 | 8.06 | 198.3 | 45.8 |
| 12 | 11.24 | 199.0 | 65.5 | 4.96 | 198.8 | 30.3 |
| 11 | 11.39 | 199.1 | 76.9 | 7.96 | 198.9 | 63.6 |
| 10 | 11.60 | 199.0 | 84.5 | 7.49 | 198.7 | 50.8 |
| 9 | 11.47 | 199.0 | 85.5 | 7.44 | 198.8 | 68.3 |
| 8 | 11.92 | 198.7 | 91.0 | 7.84 | 198.4 | 79.7 |
| 7 | 11.91 | 198.9 | 91.1 | 7.75 | 198.6 | 69.4 |
| 6 | 12.09 | 198.7 | 92.3 | 7.90 | 198.6 | 83.1 |
| 5 | 12.14 | 198.8 | 91.2 | 7.96 | 198.6 | 83.1 |
| 4 | 12.10 | 198.5 | 92.0 | 7.9 | 198.4 | 83.2 |
| 3 | 10.42 | 199.0 | 77.6 | 9.81 | 197.2 | 60.6 |
| 2 | 6.41 | 199.1 | 76.5 | 6.48 | 199.1 | 52.5 |
| 1 | 5.52 | 199.3 | 28.0 | 5.78 | 199.1 | 9.7 |

The molecular sieve column performance was consistently higher than the natural adsorbents. Adsorbent's always received identical regenerations. The molecular sieve columns operated at feed rates that were up to 46% higher than the feed rate to the corn grits. The yield of ethanol produced with molecular sieve always exceeded the natural adsorbent. The higher feed rate and yield of the molecular sieve adsorbents allows them to replace the natural adsorbent, produce more ethanol, have less recycle and reduce capital expenditure.

Figure 4:
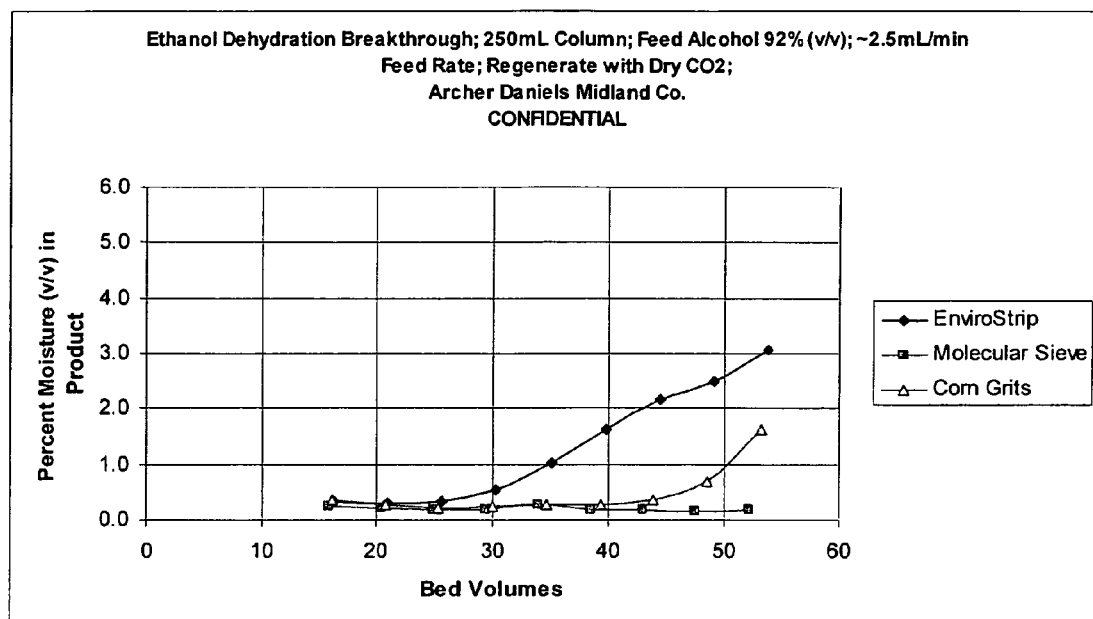
FIG. 4 shows a plot of the anhydrous ethanol percent moisture (v/v) vs. bed volumes equivalents, comparing performance of a molecular sieve absorbent vs the natural adsorbents corn grits and Envirostrip, after bed regeneration with dry $CO_2$ gas.
Figure 5:
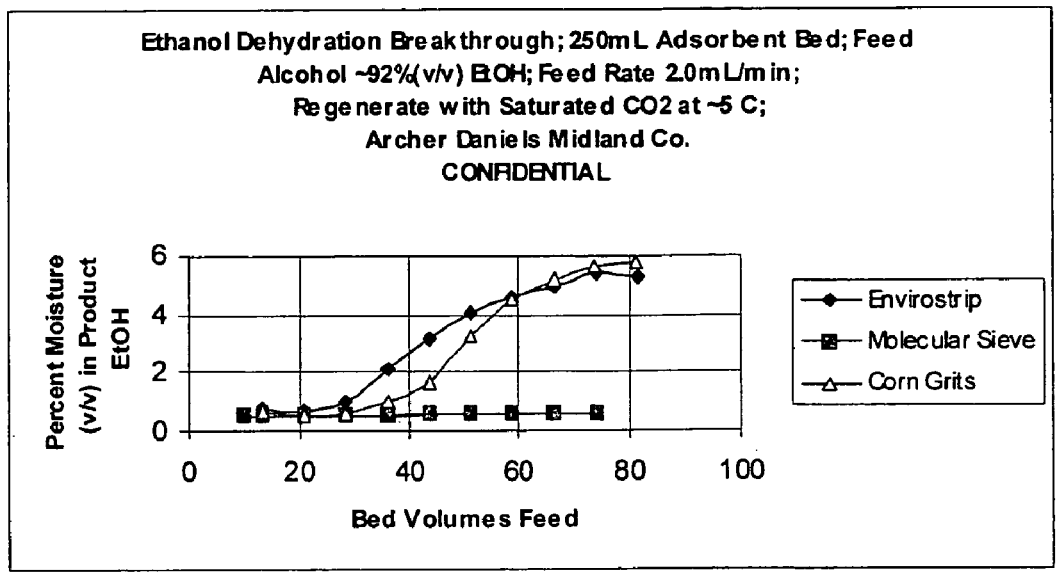
FIG. 5 shows a plot of anhydrous ethanol percent moisture (v/v) vs bed volumes equivalents, comparing a molecular sieve bed to the Envirostrip starch adsorbent bed using saturated $CO_2$ as the regenerating gas.

As seen in Table 2, Table 3, Table 4, FIG. 4 and FIG. 5—the zeolite adsorbents have greater capacity for water, than the natural adsorbents. A production increase and greater yield would be expected with larger amounts of ethanol moving forward through the zeolite adsorbents.

Whereas particular embodiments of this invention have been described for purposes of illustration, it will be evident to those persons skilled in the art that numerous variations of the details of the present teaching may be made without departing from the invention as defined in the appended claims.

What is claimed is:

1. A process for dehydrating a mixture of ethanol and water comprising,
   a) contacting a first mixture of ethanol and water with a molecular sieve bed at a first temperature in the range of 80-95° C. and at a first pressure in the range of 105-150 kPa and sufficient to urge the first mixture through the molecular sieve bed;
   b) collecting a first effluent containing ethanol having less water than the first mixture and retaining the used molecular sieve bed; and
   c) contacting the used molecular sieve bed with a carrier gas at a second temperature greater than the first temperature and in the range of 81-105° C., at a second pressure that differs from the first pressure by less than 80 kPa, to form a second effluent comprising a vapor mixture of the carrier gas, water and residual ethanol eluted from the molecular sieve bed to obtain a regenerated molecular sieve bed.

2. The process of claim 1 further including dehydrating a second mixture of ethanol and water with the regenerated molecular sieve bed.

3. The process of claim 1 wherein:
   the molecular sieve bed is a zeolite molecular sieve bed.

4. The process of claim 1 wherein the carrier gas is dried $CO_2$.

5. The process of claim 1 wherein the first temperature is about 85° C. and the second temperature is about 96° C.

6. The process of claim 1, further including
   a) collecting and cooling the second effluent to condense the water and ethanol to form a recovered dried gas and a recovered mixture of water and ethanol;
   b) combining the recovered mixture of water an ethanol with a second mixture of water and ethanol to be dehydrated; and
   c) dehydrating the combined mixture from act b using the regenerated molecular sieve bed.

7. The process of claim 1 wherein the recovered dried gas is used as the carrier gas for regenerating the molecular sieve bed.

8. A system for dehydrating ethanol according to the method of claim 1, comprising
   a) a first molecular sieve bed;
   b) a second molecular sieve bed; and
   c) control valve assemblies configured to independently switch a flow of the first mixture of ethanol/water and a flow of carrier gas between the first and second molecular sieve beds so that that at least one of the first and second sieve beds is engaged for dehydrating ethanol while the other of the molecular sieve beds is engaged for being regenerated with the carrier gas.

9. The system of claim 8 further including a condenser and control valve assemblies configured to collect and condense water and residual ethanol from an effluent of the molecular sieve bed engaged in regeneration and to route the condensed water and residual ethanol to the first molecular sieve bed engaged in dehydration.

10. The process of claim 1, wherein the direction of said carrier gas is counter to the direction of the first mixture through the molecular sieve bed.

* * * * *